US006444224B1

(12) United States Patent
Rathbone et al.

(10) Patent No.: US 6,444,224 B1
(45) Date of Patent: Sep. 3, 2002

(54) INTRA-VAGINAL DEVICE FOR PIGS

(75) Inventors: Michael John Rathbone; Shane Burccraff; James Frederick Pharaoh, all of Hamilton (NZ)

(73) Assignee: Interag, Hamilton (NZ)

( * ) Notice: Subject to any disclaimer, the term of this patent is extended or adjusted under 35 U.S.C. 154(b) by 0 days.

(21) Appl. No.: 09/424,784

(22) PCT Filed: May 27, 1998

(86) PCT No.: PCT/NZ98/00064

§ 371 (c)(1), (2), (4) Date: Mar. 2, 2000

(87) PCT Pub. No.: WO98/53758

PCT Pub. Date: Dec. 3, 1998

(30) Foreign Application Priority Data

May 28, 1997 (NZ) ............................................. 314937
Nov. 21, 1997 (NZ) ............................................. 329228

(51) Int. Cl.[7] .............................. A61F 6/06; A61F 6/00

(52) U.S. Cl. ...................... 424/486; 424/484; 424/422; 424/430; 424/423; 424/425

(58) Field of Search ................................ 424/484, 422, 424/430; 206/363

(56) References Cited

U.S. PATENT DOCUMENTS 4,881,664 A * 11/1989 Norquest et al. ........... 206/363
5,217,450 A 6/1993 Pryor et al. .............. 604/891.1

FOREIGN PATENT DOCUMENTS

| | | |
|---|---|---|
| AU | 620523 | 7/1989 |
| AU | 57961/90 | 1/1991 |
| DE | 3713404 A | * 11/1988 |
| FR | 2562797 | 10/1985 |
| GB | 2154875 | 9/1985 |
| NZ | 230023 | 7/1989 |
| WO | WO97/40776 | 11/1997 |
| WO | WO-97/40776 A1 | * 11/1997 |

* cited by examiner

*Primary Examiner*—Thurman K. Page
*Assistant Examiner*—Rachel M. Bennett
(74) *Attorney, Agent, or Firm*—Jacobson Holman, PLLC

(57) ABSTRACT

Disclosed herein is a porcine intra-vaginal device of a shape and size adapted to be positionable in the vaginal tract across the hymenal ring of a target animal (e.g., a gilt) to extend to both sides of the hymenal ring of the animal. The device once inserted delivers progesterone from a progesterone impreganated matrix on either side of the hymenal ring, the progesterone releasing surface being at least 150 $cm^2$ in total area. Variable geometry means (preferably for vestibular engagement) ensure retention of the devices (e.g., for at least 7 to 14 days) where, in the preferred device, the progesterone load of from 1.9 to 2.5 g within 1.2 mm of the release surface can, by maintaining a progesterone blood plasma level (equating to a progestrone blood plasma level in excess of 4 ng/mL measured in an ovariectomised animal), ensure or prompt the onset of oestrus within 3 to 5 days after device removal.

41 Claims, 11 Drawing Sheets

Corpora Lutea Data from Trial

Fetal Data from Trial

INTRA-VAGINAL DEVICE FOR PIGS

This application is a 371 of PCT/N298/00064 filed May 27, 1998.

TECHNICAL FIELD

The present invention relates to improvements in and/or relating to intra-vaginal devices suitable for insertion and retention within pigs.

Intra-vaginal devices are frequently used to deliver an active substance into an animal.

BACKGROUND OF THE INVENTION

One use of intra-vaginal devices is to control the breeding cycles of animals. In this respect under the trade mark CIDR™ this company has manufactured a variery of devices for different animals including but not limited to cattle, sheep and pigs. The prior art devices of this company where they are to be used to synchronise oestrus have usually involved a spine (for example of a nylon plastics material) and an at least partially encasing silicone rubber matrix that has been impregnated with the active substance to be released, eg. progesterone.

The prior art device of this company marketed under the trade mark CIDR™ for pigs is detailed in New Zealand Letters Patent No. 230023 of which the Australian and U.S. equivalents are respectively numbers AUS620523 and U.S. Pat. No. 5,217,450. Appended hereto in the annexed drawings (FIGS. 4A to 4C) are representations of such a prior art form from which it will be seen that a complex construction having wall engaging means at each end has been hitherto required in order to obtain a good measure of retention. In addition a complex construction for the non cervix end was required whereby the retention device at that end could be configured in three different ways, only one of which was its retention condition.

With pigs a great deal of care is required in order to ensure retention against spontaneous ejection and also against withdrawal by another animal.

The full content of the aforementioned patent specifications are hereby here included by way of reference.

The literature adequately explains the purposes for which such intra-vaginal devices containing progesterone or progestagens are delivered into female animals prior to mating.

In addition reference should be made, by way of example, to proprietary information released by suppliers of such active substances including, by way of example, VIRBAC in respect of its SUIPROST™ injectable product which is a synthetic prostaglandin for induction and synchronisation of farrowing in sows. The role however of such intra-vaginal devices usually is to be much earlier, namely, in respect of synchronising the onset of oestrus.

If both the control of oestrus cycle and high fertility are desired in the pigs then an intra-vaginal insert must deliver sufficient progesterone. We know that 15, 25, 50 mg per day (IM) for 14 days results in control of the oestrus cycle. However poor fertility results. We believe a dose of 100 mg per day for 14 days (IM) is desirable to both control the oestrus cycle and give normal fertility.

The present invention is therefore directed to porcine intra-vaginal devices that feature an improved retention characteristic (eg; across hymenal ring positioning and vestibular deployment of retention means), is of sufficient surface area as far as progesterone impregnated matrix or matrices is concerned and/or can deliver progesterone (at least) on both sides of the hymenal ring.

The amount of progesterone delivered by the said device preferably should be at least sufficient to maintain a plasma level of in excess of 4 ng/mL (as measured in an ovariectomised animal over at least a 14 day insertion period).

The present invention in one aspect is directed toward an intra-vaginal device which provides an alternative to the aforementioned prior art device. A preferred device is believed to provide a simplicity of moulding in at least some of its forms whilst providing in such preferred forms enhanced retention characteristics irrespective of the variations within the vaginal tracts of different pigs.

The present invention in other aspects relates to the control of the onset of oestrus and/or the maintenance or enhancement of fertility of pigs (particularly gilts).

BRIEF SUMMARY OF THE INVENTION

In a first aspect the invention consists in a porcine intra-vaginal device of a shape and size adapted to be positionable in the vaginal tract across the hymenal ring of a target animal (eg; a gilt) to extend to both sides of the hymenal ring of the animal, the device having or being (at least in part) a progesterone impregnated matrix or matrices to be on at least either side of the hymenal ring and being at least 150 $cm^2$ in total area.

Preferably said total area of progesterone impregnated matrix or matrices is greater than 172 $cm^2$.

Preferably said matrix or matrices carry a progesterone load of at least 1.9 g.

Preferably said progesterone load is from 1.9 to 2.5 g.

Preferably, for gilts, said progesterone load is about 2.2 g.

Preferably said progesterone load is at least substantially all carried by the matrix or matrices within 1.2 mm of its release surface.

Preferably the device has a nylon (or equivalent) spine with an impregnated matrix formed thereabout.

Preferably the device has variable geometry means which deploy or is deployable upon insertion to retain the device in the vaginal tract. The variable geometry means may deploy on either or both sides of the hymenal ring.

Preferably the variable geometry means comprise at least one resilient wing or a form collapsible under the action of withdrawal.

Preferably the device is elongate of body with a wasted region to lie on the hymenal ring.

Preferably the matrix is a progesterone containing silicone rubber material which has been formed by injection of the uncured progesterone containing matrix as a liquid into a mould for a sufficient time to achieve a mould temperature or temperatures within the range of from 100° C. to 210° C. and a shape retaining at least partial cure thereof.

In a second aspect the invention consists in a porcine intra-vaginal device of a shape and size adapted to be positionable in the vaginal tract across the hymenal ring of a target animal (eg; a gilt) to extend to both sides of the hymenal ring of the animal, the device having or being (at least in part) a progesterone impregnated matrix or matrices to be on at least either side of the hymenal ring, the device having variable geometry means which deploy in the vestibule upon insertion to retain the device in the vaginal tract.

Preferably said matrix or matrices are at least 150 $cm^2$ in total area.

Preferably said total area of progesterone impregnated matrix or matrices is greater than 172 $cm^2$.

Preferably said matrix or matrices carry a progesterone load of at least 1.9 g.

Preferably said progesterone load is from 1.9 to 2.5 g.

Preferably, for gilts, said progesterone load is about 2.2 g.

Preferably said progesterone load is at least substantially all carried by the matrix or matrices within 1.2 mm of its release surface.

Preferably the device has a nylon (or equivalent) spine with an impregnated matrix formed thereabout.

Preferably the matrix is a progesterone containing silicone rubber material which has been formed by injection of the uncured progesterone containing matrix as a liquid into a mould for a sufficient time to achieve a mould temperature or temperatures within the range of from 100° C. to 210° C. and a shape retaining at least partial cure thereof.

In another aspect the present invention consists in an intra-vaginal device having an elongate body (preferably not articulated) to be inserted in a pig with part on either side of the hymenal ring of a pig and having variable geometry retention means dependent from that part of the elongate body to be located in the vestibule of the vaginal tract, said variable geometry retention means being capable of assuming a vestibule engagement form after release from an insertion mode.

Preferably said vestibule geometry retention means is or are capable of assuming a third mode, ie. a withdrawal mode upon the application of an external force to part of said device within said vestibule or to any means dependent therefrom extending towards and/or through the vulva.

Preferably said variable geometry retention means are in the form of wing members.

Preferably said resilient members are in the forms of wings which assume in their vestibular engagement mode a condition such that spasm of the vestibular wall of an animal into which the device has been inserted is unlikely to provide a sufficient component of force on the inserted device to cause ejection from the vaginal tract.

Preferably said variable geometry retention means in said vestibular engagement mode engages into folds at least momentarily present in the vestibule wall of the animal into which it has been inserted.

Preferably the variable geometry retention means is such that spasm of the vaginal tracts and in particular the vestibule of the animal into which the device has been inserted is such as to provide no significant net force away from the cervix on the device.

Preferably with a view to meeting the aforementioned functional requirements concerning retention, most preferably the variable geometry retention means is in the form of wings (preferably two, which are preferably opposed), each of which, in its deployed vestibular engagement mode, has a distal end closer to the vulva than that region of that part of the elongate body of the device from which that particular wing projects.

Preferably the device includes a reduced section or an effective reduced section (if for example the device is fluted or otherwise) over that region of the elongate body of the device adjacent the variable geometry retention means dependent therefrom but which is adapted to lie within the hymenal ring of the animal when the device is in its retained condition.

Preferably the device or at least parts thereof (for example at least the vaginally received part of the elongate body carries or is a matrix impregnated with or carrying a substance to be released to the animal.

Preferably the construction of the device is such that it does not extend into the cervix during normal insertion operations and such that upon normal insertion where it is retained by said variable geometry retention means such variable geometry retention means and/or the configuration of the elongate body of the device is such as to prevent sufficient movement through the hymenal ring to allow the end of the device to enter the cervix.

Preferably that part of the elongate body which carries the variable geometry retention means includes means capable of being engaged by a device withdrawal tool (or by other means).

Preferably the device is one that includes at least one or more of the following parameters (i) at least a surface area greater than 180 $cm^2$ of a progesterone impregnated matrix, (ii) a length of from 9.0 cm to 15.0 cm (and preferably about 11.0 cm) for that region to extend during normal use in a pig from the hymenal ring towards the cervix and/or to extend for a distance of from 4.5 cm to 8.0 cm (preferably about 5.5 cm) during normal use from the hymenal ring to the vulva opening, (iii) a maximum cross-sectional area (other than in respect of the variable geometry retention means) of from 2.5 $cm^2$ to 4.5 $cm^2$, (iv) a reduction in cross-sectional area for that region of the elongate body adapted to be positioned at the hymenal ring so as to have a maximum cross sectional dimension of from 1.5 cm to 3.5 cm (preferably about 2.5 cm), (v) at least one flute or the like providing form provided in that zone to be positioned in the vestibule, (vi) at least one opening in at least one of the flute forming shapes to allow the insertion of a withdrawal tool, (vii) at least one flute or the like providing form extending longitudinally of that region of the elongate body to be located within the vagina proper.

Preferably the loading of the impregnated matrix is with from 1.9 to 2.5 grams of progesterone (preferably about 2.0 grams progesterone).

Irrespective of the loading or surface area of the device and/or the depth of any impregnated matrix (whether an encasing matrix on a structural spine or not, or a shape holding impregnated matrix itself without a separate spine) it is capable over a period of from 7 to 14 days in an average gilt being prepared for the onset of oestrus upon withdrawal of the device of maintaining a blood plasma level equating to a blood plasma level in excess of 4 ng/mL measured in an ovarectomised animal.

In a different aspect the invention consists in an intra-vaginal device for delivering a substance into a pig (preferably at least substantially via the vaginal mucous and membrane), said device comprising an elongate body (preferably non articulating) having a withdrawal end and an insertion and capable of traversing the hymenal ring of the pig with the withdrawal end in the vestibule and the insertion end in the vaginal cavity, and at least one wing like structure capable of self deployment (e.g. resiliently) from an insertion condition into a membrane engaging condition to resist spontaneous ejection of the device, the membrane being selected from one or more of (i) vestibular membrane, (ii) hymenal ring membrane, and (iii) vaginal membrane.

Preferably said device is one as previously defined in any of its forms.

In yet a further aspect the present invention consists in a pack which includes a plurality of intra-vaginal devices in accordance with the present invention and preferably also at least one applicator and/or withdrawal tool therefor.

Preferably said pack includes directions of use.

In yet a further aspect the present invention consists in a method of delivering a substance into a female pig which comprises inserting a device as previously defined into the vaginal tract of the pig so as to release a substance from the device whilst resident therein, the device resisting spontaneous ejection by means of the deployment of said variable geometry retention means (preferably within the vestibule so as to engage the wall or walls thereof).

Preferably said device is as defined in any of its forms previously described and is inserted in a female pig (eg gilt) for a period of from 7 to 18 days where it maintains substantially over its insertion period a blood plasma level of progesterone equating to a progesterone blood plasma level in excess of 4 ng/mL measured in an ovariectomised animal, and whereupon, upon its withdrawal, will ensure within 3 to 5 days thereafter the onset of oestrus in the female pig.

Preferably the withdrawal is achieved by hooking a tool wire or other apparatus into the vestibular end region of the device and withdrawing the same.

Preferably said device is not capable of normally being reached by another pig once correctly inserted in a pig.

Preferably said device is inserted while at least having the variable retention means temporarily constrained to lie against part of the elongate body.

Preferably said variable geometry retention means are wings that during normal insertion and normal retention are angled from the elongate body with their distal ends nearer the vulva than those ends connected to the elongate body but (preferably) which pass over a condition substantially normal to the elongate axis of the elongate body of the device at the time of or during withdrawal so as to angle more towards the hymenal ring than to the vulva.

Preferably the method involves positioning the device such that a reduced section along the length of the elongate body of the device is in the zone of the hymenal ring and the variable geometry retention means is in the vestibule but may on occasions nevertheless result in retention being achieved with the variable geometry retention device accidentally having been inserted on the vaginal side of the hymenal ring (or at least the device has that capability) at least until moved under action of the pig to properly deploy the variable geometry retention means within the vestibule.

In a further aspect the present invention consists in, in a number of female pigs, the act of at least inserting and retaining for a period of time (and optionally removing the same prior to slaughter, eg. as might be required for mating or farrowing) a device as previously defined and wherein at least a majority of the devices are inserted such that said variable geometry retention means deploys and engages the wall of the vestibule between the vulva entrance and the hymenal ring rather than the hymenal ring itself or the vaginal wall on the vaginal side of the hymenal ring.

In still a further aspect the present invention consists in a plurality of female pigs each which has had a device as previously defined inserted into the vaginal cavity thereof by a method in accordance with the present invention.

Preferably said pigs have a progesterone blood serum level whilst the device is resident in their vaginal tract equating to a blood plasma level in excess of 4 ng/mL measured in an ovarectomised animal.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF DRAWINGS

Preferred forms of the present invention will now be described with reference to the accompanying drawings in which.

DETAILED DESCRIPTION

Figure 1:
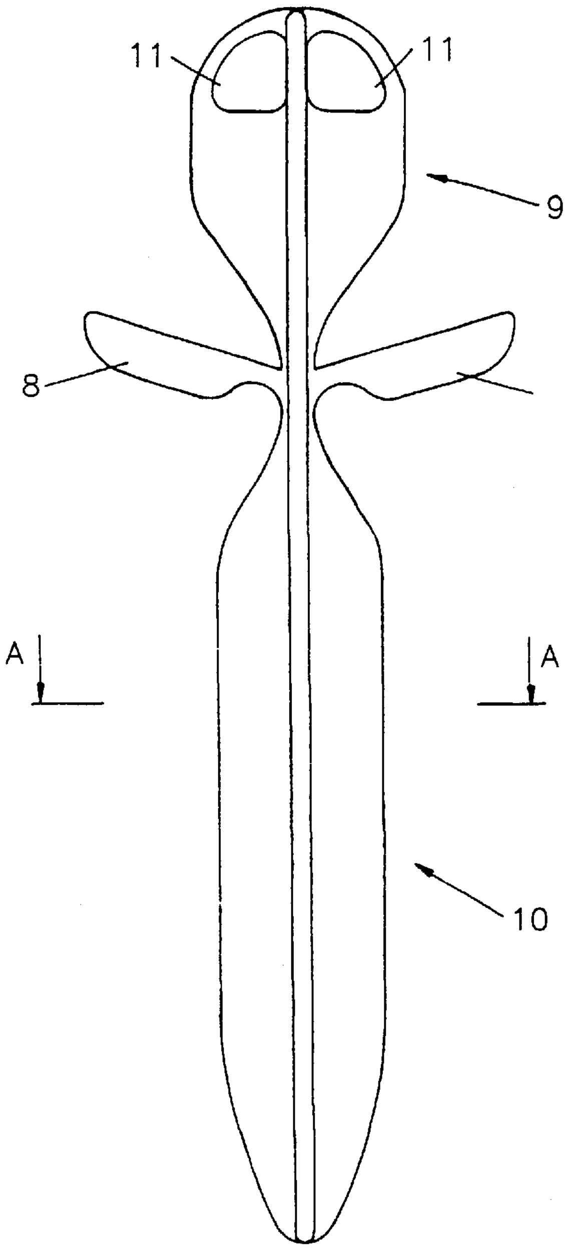
FIG. 1 is a side elevation of a preferred device in accordance with the present invention showing two opposed wings capable of flexibly moving to lie in either direction in the plane of the drawing to lie against the elongate body from or adjacent the reduced hymenal ring region of the device as better explained by reference to FIGS. 3A to FIGS. 3C, FIG. 1 showing a fluted cross-sectional form in the longitudinal axis preferably for both the vestibular and vaginal regions of the elongate body and preferably also the hymenal ring reduced cross-sectional area.

Considerable need has existed for many years for the availability of an effective means to control the occurrence of oestrus and ovulation in pigs. The primary research approach has been to develop a pharmaceutical with the capability to block ovarian activity so that animals in a group at various stages of reproduction would complete the oestrus cycle, including regression of corpora lutea, and then the only block to follicular growth, oestrus, and ovulation would be the compound being administered. In addition, the various compounds that have shown the most promise to meet this need were orally effective and administered once daily at feeding. Two specific compounds found to be effective for this purpose have been methallibure (AIMAX®) and altrenogest (Regumate®). However, neither of these compounds have been made available to pig producers in the United States and the need for an effective method to control the reproductive cycle in pigs continues to exist.

One may ask the question, "Why is there a need in pig production to be able to predict the occurrence of oestrus and ovulation?". Perhaps the number one reason is to be able to couple synchronisation of oestrus and artificial insemination (AI). In that regard the need has increased recently because of the dramatic increase in use of AI in swine in the U.S. during the past 5 to 10 years from a use of less than 5% to a level frequently estimated to be 35 to 40% at present. In addition, most pig production confinement units desire to use an "all in, all out" system or operation, ie; all animals moved into a specialised unit, such as breeding, farrowing, nursery, etc. of the production cycle, are moved in and out at the same time. To have the animals grouped closely enough to follow this practice starts at the time of breeding and hence the requirement for control of oestrus and ovulation, particularly in gilts.

Further, other technologies can be implemented more effectively when animals in a group are of similar ages and/or reproductive status. For example, induced farrowing and cross-nursing of newborn pigs can be performed more effectively as can vaccinations, marketing, etc.

A need also exists among researches for an effective method to modify the oestrus cycle when using technologies requiring the collection of embryos, AI, embryo transfer, studies or follicular development, as well as related studies that desire closely grouped farrowing dates for nutrition experiments, etc. Studies that require precise prediction of reproductive state for collection of timed embryos of a given stage of development would benefit immensely from the availability of this technology and require fewer experimental animals to complete statistically valid studies.

Rather than synthetic compounds that are orally effective and administered at prescribed doses on a daily basis, we favour the use of the natural compound, namely progesterone, that regulates the occurrence of ovaries cyclicity in vivo and is administered continuously during a prescribed 14 day period using an intra-vaginal device. The design of the device ideally is unlike intra-vaginal devices being used for cattle and sheep to control oestrus. This is of particular note since previous attempts to use intra-vaginal sponges and other devices have been largely ineffective in pigs due to lack of a high rate of retention and also due to other animals extracting the devices by pulling on external attachments used to remove the insert at the end of the treatment period.

Figure 4A:
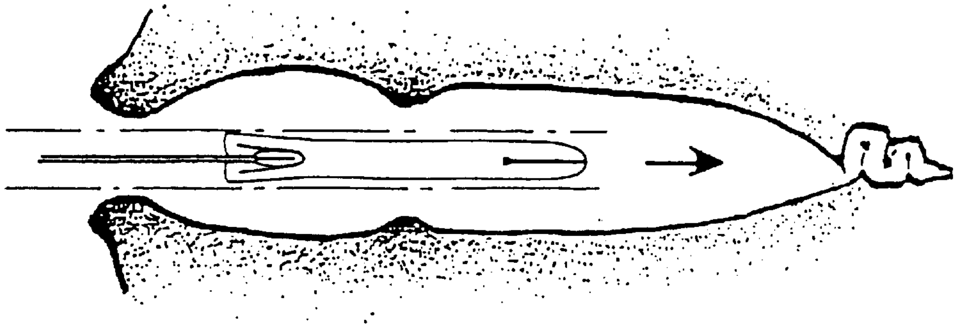
FIG. 4A (PRIOR ART)
FIG. 4A through 4C show corresponding drawings to FIGS. 3A to FIGS. 3C but in respect of the prior art device of our aforementioned patent specifications, the device showing the more complex deployment required, such deployment being intended and achieved solely in the vagina itself.
Figure 4B:
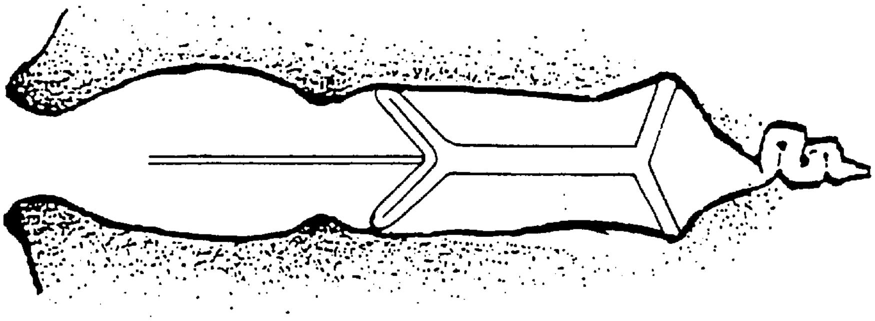
FIG. 4B (PRIOR ART)
Figure 4C:
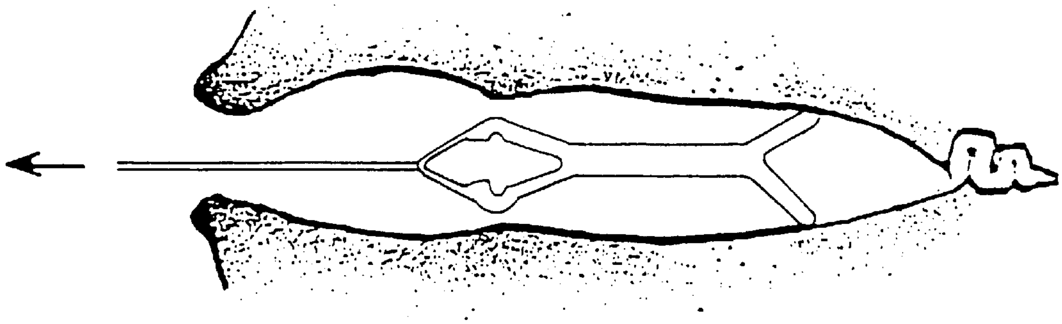
FIG. 4C (PRIOR ART)

Control of the oestrus cycle of gilts is achieved by the use of progesterone impregnated devices such as our prior art device depicted in FIG. 4A to 4C. See Table 1. Such a prior art device as trialed had a surface area of 100 $cm^2$.

TABLE 1

Mating and farrowing rates for untreated and our prior art device treated gilts.

| | Control | CIDR | Sig(Chi sq) |
|---|---|---|---|
| Total number of gilts | 162 | 139 | |
| Number of gilts on heat and mated | 145 | 123 | NS |
| % Mated | 89.5% | 88.5% | |
| No. of gilts farrowed | 127 | 60 | p < 0.001 |
| Farrowing rate | 87.6% | 48.8% | |
| Average first mating age | 219.4 | 218.4 | NS |
| Av Born alive/litter | 8.91 | 8.72 | NS |
| Av Total born/litter | 9.58 | 9.58 | NS |

The results from Table 1 show that the treatment using the prior art device had a significant effect on animals coming on heat or average number of piglets born. Examination of the ovaries of the test animals revealed that a great number of the test animals had developed large numbers of cysts on their ovaries.

The negative effect on fertility we believe arises from a failure to maintain sufficiently high blood progesterone levels in some individuals.

Retention of the prior art device was 82% in a study which used 130 maiden gilts. By comparison retention of the preferred device of the present invention in a total of 37 test gilts for 14 days was 100%.

Subsequent work by us using multiple prior art devices inserted into the vagina of maiden gilts showed that between 3 to 4 such devices were needed to prevent cyst formation on ovaries.

In our research we have determined there is a good relationship between amount of progesterone delivered and the surface area of device (see our PCT/NZ97/00052). The larger the surface area the more progesterone that is released and the higher the resultant plasma levels.

Since the surface area of the prior art device was 100 $cm^2$, extrapolation would suggest that a single insert with at least 300 $cm^2$ would be needed to deliver the required amount of progesterone into a pig for efficacy. This would appear to make the development of a device for the control of oestrus in pigs without a negative effect of fertility not feasible because of the physical size of the pigs vagina. However we determined when 3 or 4 devices are simultaneously administered such devices overlap thereby preventing some of their surface area from releasing progesterone. Therefore we came to believe that a smaller surface than 300 $cm^2$ may be sufficient for efficacy.

We now believe 150 $cm^2$ to be a minimum where there is delivery on either side of the hymenal ring. More preferably the area should be 180 $cm^2$ or above.

The prior art device non use of the vulval area of course greatly restricted the area available for drug delivery.

To develop a device of this surface area extensive studies were undertaken to model the shape and dimensions of the pigs vagina so that a shape could be designed that would be retained comfortably inside the vagina and would also utilize both the vagina and vulva for drug delivery to thereby maximise uptake of progesterone from any available release surface of the impregnated matrix or matrices.

If both the control of oestrus cycle and high fertility are desired in the pigs then an intra-vaginal insert must deliver sufficient progesterone. We know that 15, 25, 50 mg per day (IM) for 14 days results in control of the oestrus cycle. However poor fertility results. We believe a dose of 100 mg per day for 14 days (IM) is desirable to both control the oestrus cycle and give normal fertility.

We have determined that an intra-vaginal device which released about 0.7 g of progesterone over a 14 day period was sufficient to control the oestrus cycle (time of heat), yet was insufficient to give good fertility.

A preferred device with the following dimensions was developed from shape development studies:

(i) at least a surface area greater than 180 $cm^2$ of a progesterone impregnated matrix, (ii) a length of from 9.0 cm to 15.0 cm (and preferably about 11.0 cm) for that region to extend during normal use in a pig from the hymenal ring towards the cervix and/or to extend for a distance of from 4.5 cm to 8.0 cm (preferably about 5.5 cm) during normal use from the hymenal ring to the vulva opening, (iii) a maximum cross-sectional area (other than in respect of the variable geometry retention means) of from 2.5 cm to 4.5 cm, (iv) a reduction in cross-sectional area for that region of the elongate body adapted to be positioned at the hymenal ring so as to have a maximum cross sectional dimension of from 1.5 cm to 3.5 cm (preferably about 2.5 cm), (v) at least one flute or the like providing form provided in that zone to be positioned in the vestibule, (vi) at least one opening in at least one of the flute forming shapes to allow the insertion of a withdrawal tool, (vii) at least one flute or the like providing form extending longitudinally of that region of the elongate body to be located within the vagina proper.

Preferably the loading of the impregnated matrix is with from 1.9 to 2.5 grams of progesterone (preferably about 2.0 progesterone).

Figure 3A:
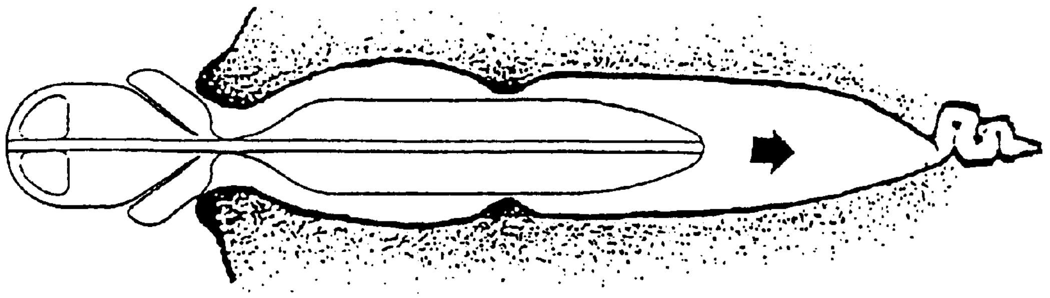
FIGS. 3A shows the insertion of a device (not showing any insertion tool) into a vaginal tract.
Figure 3B:
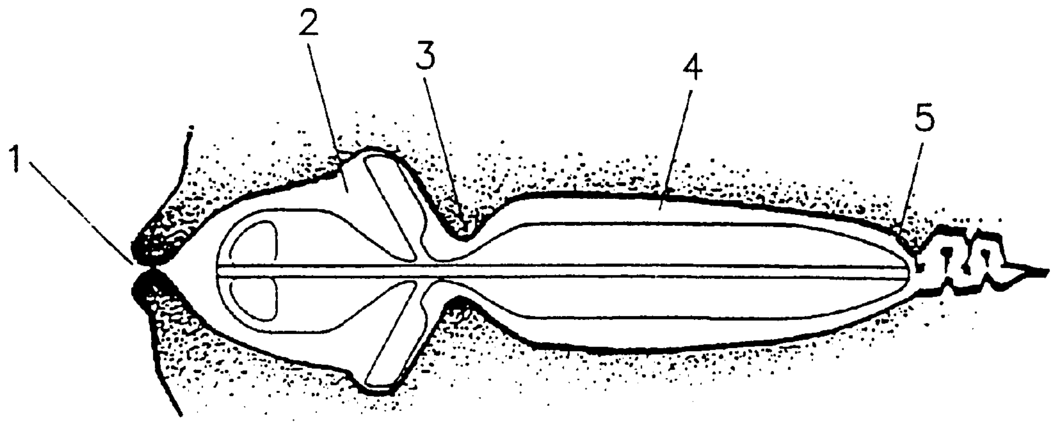
FIG. 3B shows the device properly deployed with the variable geometry retention means in the vestibule.
Figure 3C:
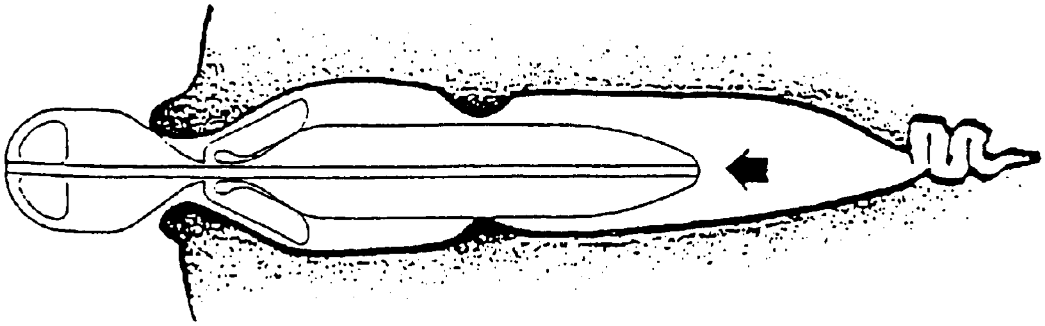
FIGS. 3C shows the device during withdrawal with preferably two opposed wings assuming a different angling to that of such wings both during insertion and deployment to facilitate withdrawal.

In FIG. 3 there is shown by reference numerals 1 through 5 the following zones or positions of the vaginal tract of a female pig.

1. The vulva entrance.

2. The vestibule.

3. The hymeneal ring.

4. The vagina.

5. The cervical entrance.

The preferred device of the present invention is an easily moulded form capable of being moulded initially with a nylon spine 6 about which there is then moulded or fabricated an encasement of progesterone impregnated silicone rubber 7.

The active ingredient of the device is micronised USP natural progesterone. Device potency is determined by the percentage of active ingredient present in the inactive silicone elastomer.

The progesterone is mixed into each of two liquid silicone parts prior to the silicone being introduced to the machine for moulding. A suitable two liquid system is that of Dow Coming Co marketed as Q74840 parts A and B.

At the moulding stage the two parts of the liquid silicone are pumped under pressure of approximately 100 bar from pails into the injection chambers of an injection moulding machine. Upon injection, the two parts of silicone are simultaneously forced through a static mixer before flowing into an electrically heated mould.

The nylon spine is inserted into the mould prior to the silicone being injected. The mould has a die surface temperature of typically 190°–150° C., but preferably never exceeding 200° C. The mould is kept clamped shut under approximately 30 tonnes of static pressure while the silicone cures. At the indicated temperature and pressure, the liquid silicone takes approximately 50 seconds to cure into a rubber.

Following curing, the finished product is removed from the mould and cooled before packaging.

Preferably the wings 8 (FIG. 1), the vestibular region 9 (FIG. 1) and the vaginal region 10 (FIG. 1) are all provided with the silicone/progesterone matrix 7 (FIG. 2) encasement.

As can be seen from FIGS. 3A the wings 8 (FIG. 1) preferably angle back onto the vestibular region 9 (FIG. 1) of the device to allow easy insertion (with or without a retaining sleeve or the like which would form part of an applicator tool). A simple piston including sleeve is all that would be required to constrain the wings 8 (FIG. 1) in the condition shown in FIG. 3A during insertion and to thereafter allow the withdrawal of the tool by a piston expressing the device from the sleeve during withdrawal of the insertion tool.

Upon appropriate deportment as shown in FIGS. 3B the wings 8 (FIG. 1) push into the membrane (possibly even into the folds of vestibular cavity walls).

In some other maladministered forms the deployment may instead be on the vaginal side of the hymenal ring 3 (FIG. 3B). In such poorly inserted forms nevertheless there will be retention in most cases.

The present invention however has found a surprising increase in ease of use and in retention performance with a device of a kind broadly described hereinbefore where the intended variable geometry retention is within the vestibule region rather than elsewhere. Such a device also allows the inclusion within the vestibule (a naturally self flushing region of the vaginal tract, ie. by urine) of a withdrawal opening or openings 11 (FIG. 1) which when located in at least two parts of a fluted structure as depicted quickly receive a hook or the like withdrawal tool (not shown) there into under the action of the vanes that define the flute form that is carried throughout the device.

While a flute form has been described, obviously spiral, cylindrical (perforate or skeletal) and other forms for defining at least parts of the elongate body can be used as can other deployable variable geometry retention means beyond the proposed simple opposed wing structure. It is found however that the form as depicted lends itself readily to firstly moulding of the nylon or other main structural frame components and thereafter the moulding thereon of the impregnated matrix.

Figure 10A:
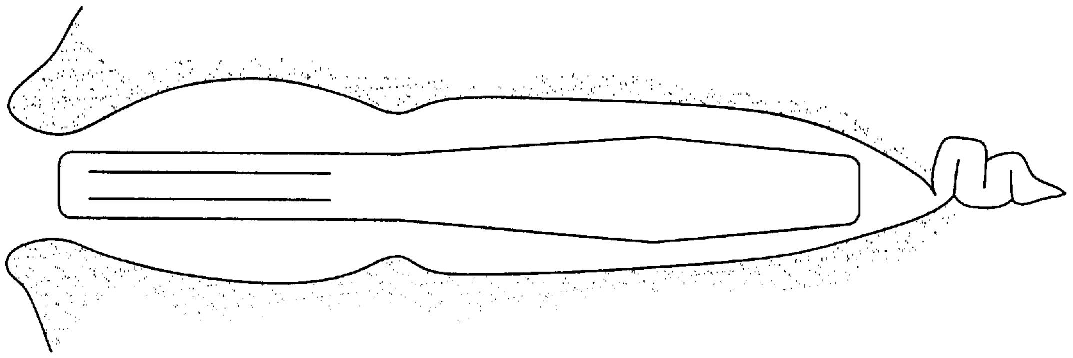
FIG. 10A and 10B show in a similar way to FIGS. 3A through 3C and 4A through 4C a different form of variable geometry device for vestibular deployment, such means upon withdrawal forces returning almost to an insertion type condition.
Figure 10B:
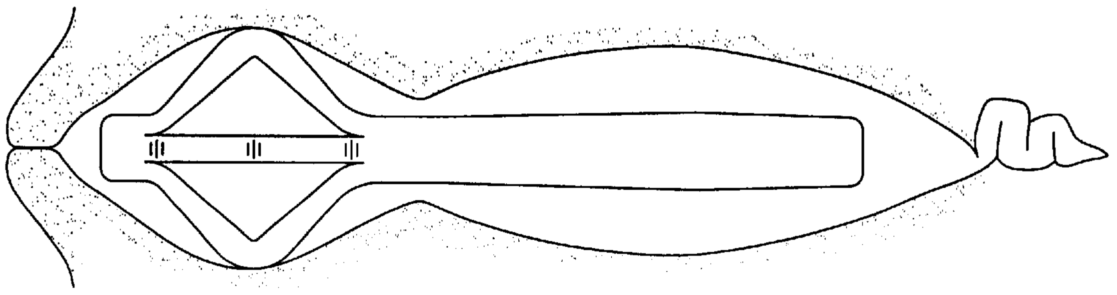
Figure 11A:
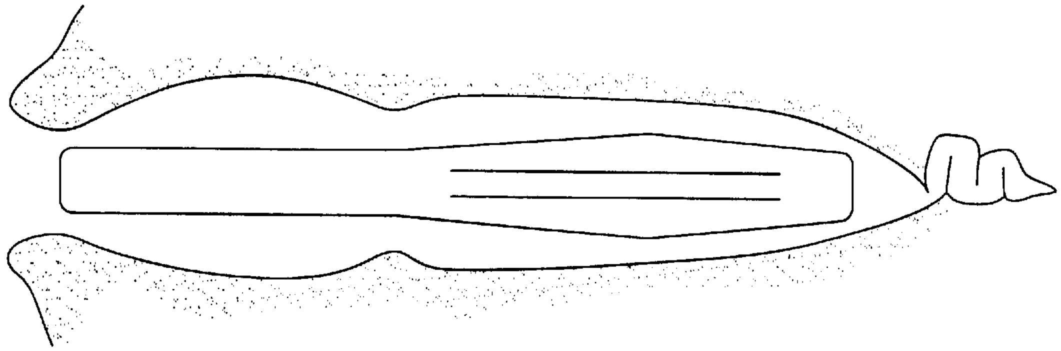
FIGS. 11A and 11B show how a deployable arrangement as in FIGS. 10A and 10B may instead (or even in addition) deploy on the vaginal side of the hymenal ring.
Figure 11B:
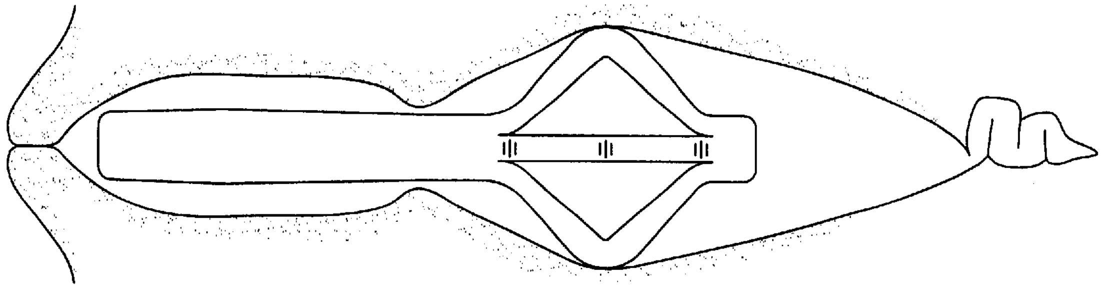

However forms of variable geometry deployment may vary. See the more easily withdrawable options of FIGS. 10A and 11B and 11A and B, the devices being deployed in FIGS. 10B and 11B. Obviously hybrids are also possible.

Examples of materials that might be used for the spine and/or the initial part of the body include nylon and polyester.

Examples of materials that might be used include to carry the progesterone are silicone, polycaprolactone, EVA, starch derivatives and polyesters.

The most preferred device is the device of FIGS. 5A through 5F is of a form and size as depicted in FIGS. 5A through 5D. It comprises a flat spine of nylon about which is moulded an active ingredient impregnated matrix of a silicone rubber. Appropriate materials and loadings and active ingredients are those discussed inter alia in our PCT/NZ97/00052 (published as WO 97/40776). Obviously other types of active ingredient and intra-vaginal uses for such a device abound.

The present invention also envisages non spined versions of such a device.

Figure 2:
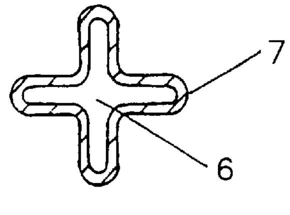
FIG. 2 is a cross-sectional view in the direction of AA shown on FIG. 1, the cross-section showing the presence of a preferred spinal structure (for example of nylon) and a layer of a progesterone or other active substance impregnated matrix positioned thereon.
Figure 5A:
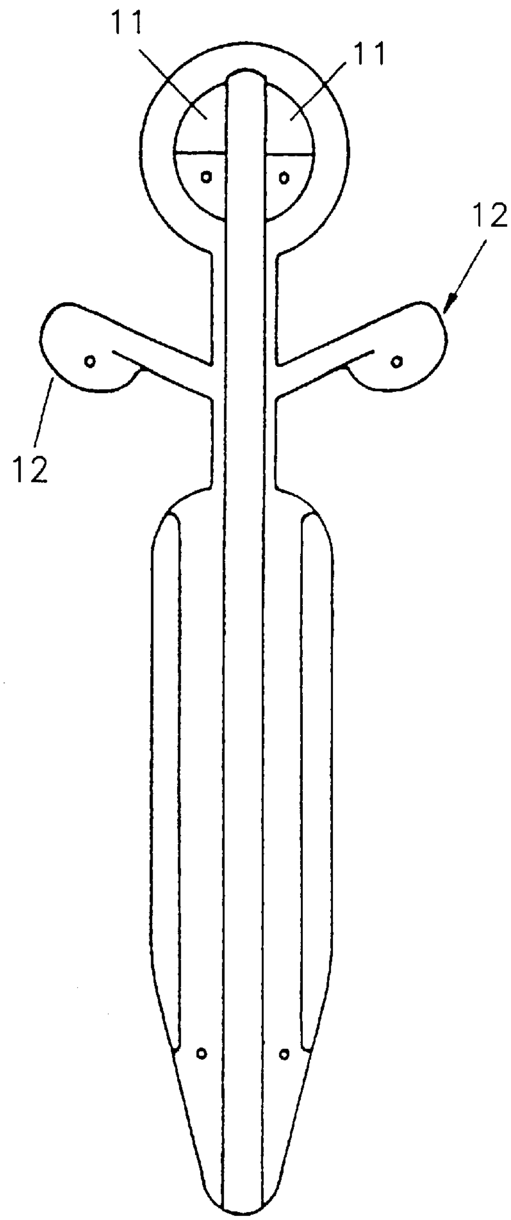
FIGS. 5A through 5F show a most preferred device in accordance with the present invention.
Figure 5B:
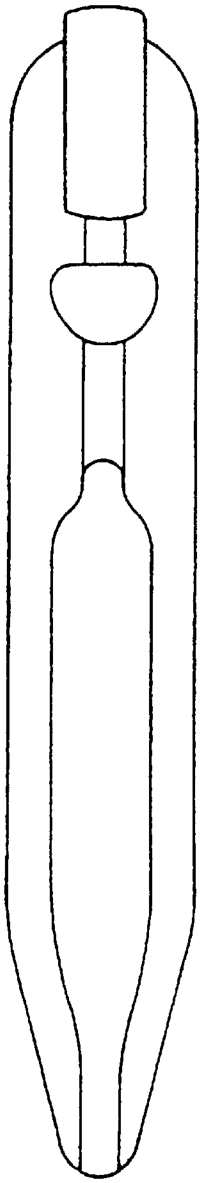

FIG. 5A is one side view showing openings 11 (FIG. 1) which facilitate the withdrawal of the device, such openings serving a similar function to those also indicated as 11 (FIG. 1) in FIG. 1. FIG. 5B is another side view of the device of FIG. 5A but rotated by 90°.

Figure 5C:
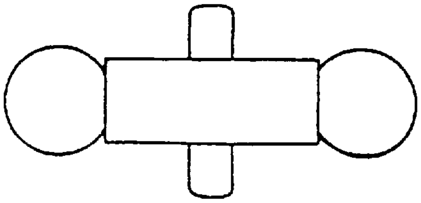
Figure 5D:
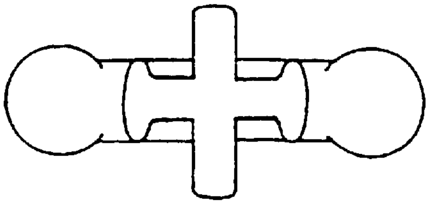

FIG. 5C is a top view of the device depicted in FIG. 5A while FIG. 5D is a bottom view of the device depicted in FIG. 5A.

Figure 5E:
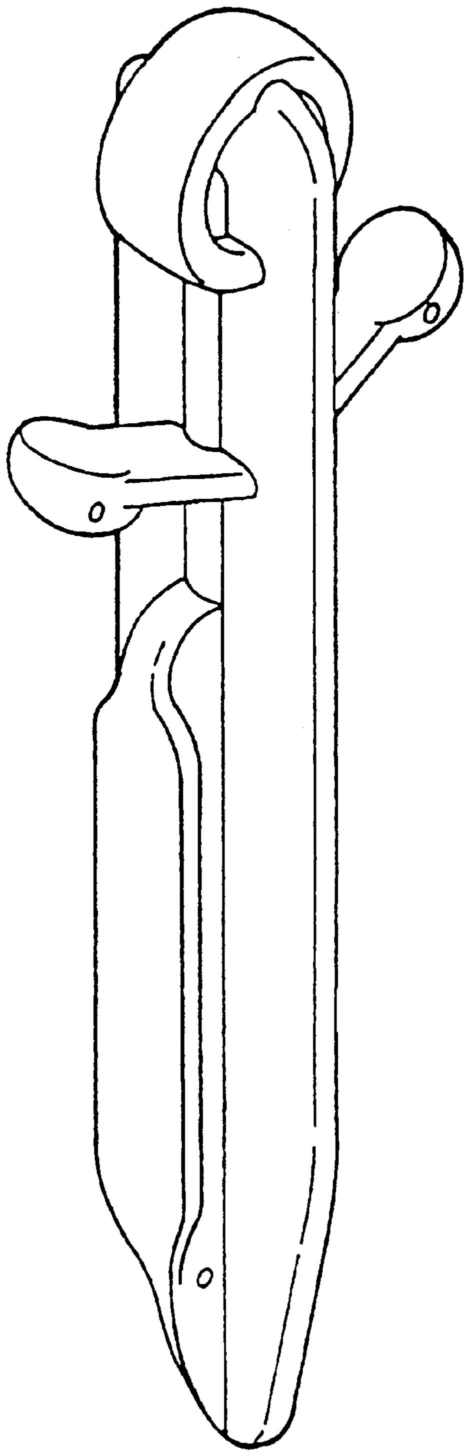
Figure 5F:
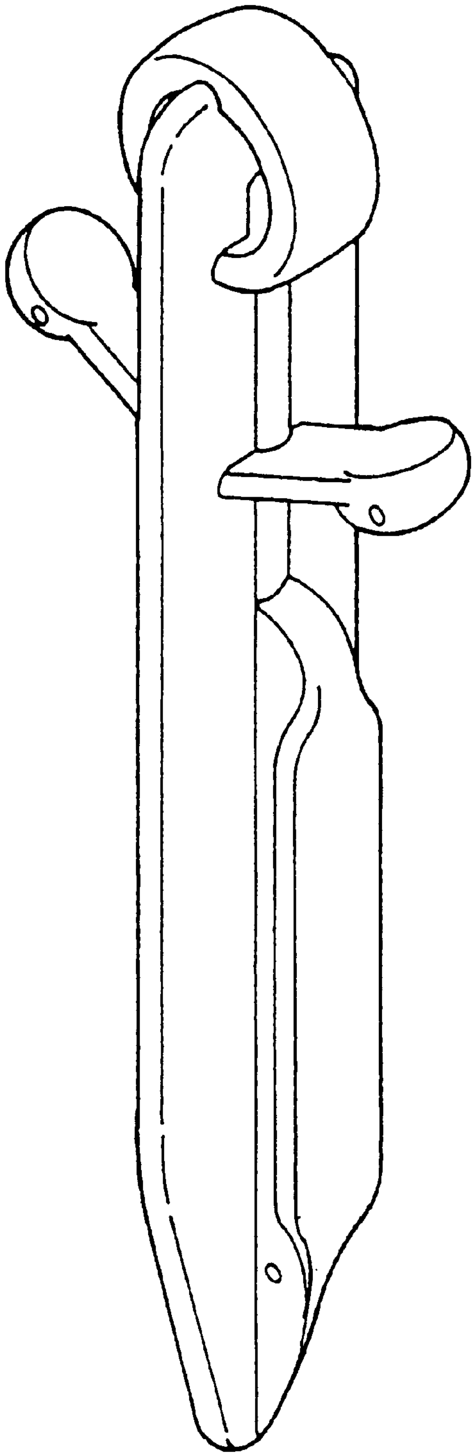

FIGS. 5E and 5F are perspective views of the device.

In other forms of the device the wing like protuberances 12 (FIG. 5A) (which preferably have the angular deposition as depicted) may be more at right angles or indeed may even be angled towards the lower end.

As can be seen however every attempt has been to provide smooth corners and edges so as to minimise trauma to any part of the animal during its insertion, its retention and its withdrawal.

The device as depicted in FIG. 1 with a progesterone loading of 2.7 g in a silicone skin of less than or about 2.5 mm deep and an area of 180 $cm^2$ was then used in trial work to examine its efficacy. The following is data derived from the efficacy studies.

Figure 6:
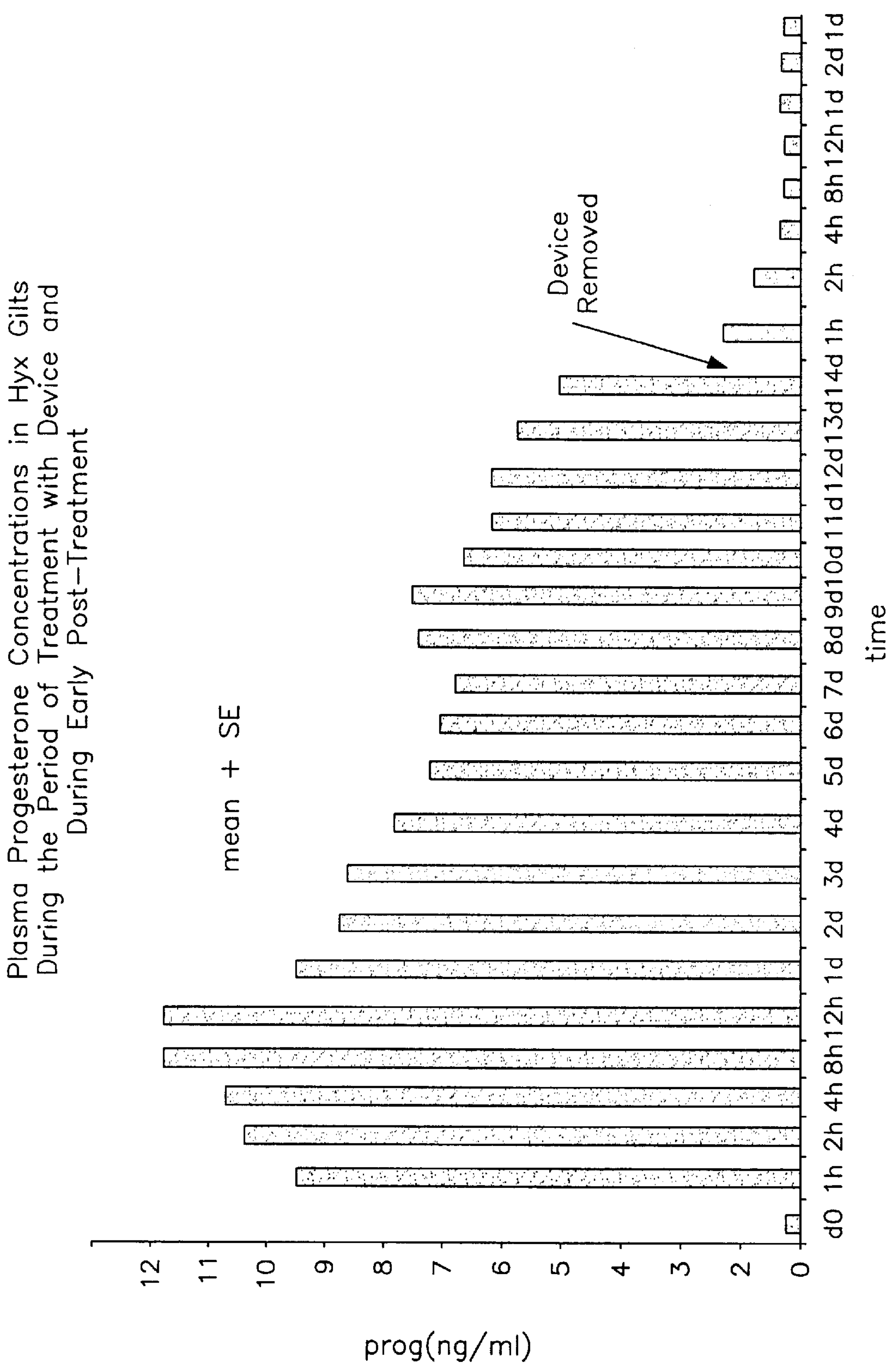
FIG. 6 is a plot of plasma progesterone levels (ng/mL) against time in Hyx Gilts for the device of the present invention (ie; as depicted in FIGS. 5A to 5F).
Figure 7:
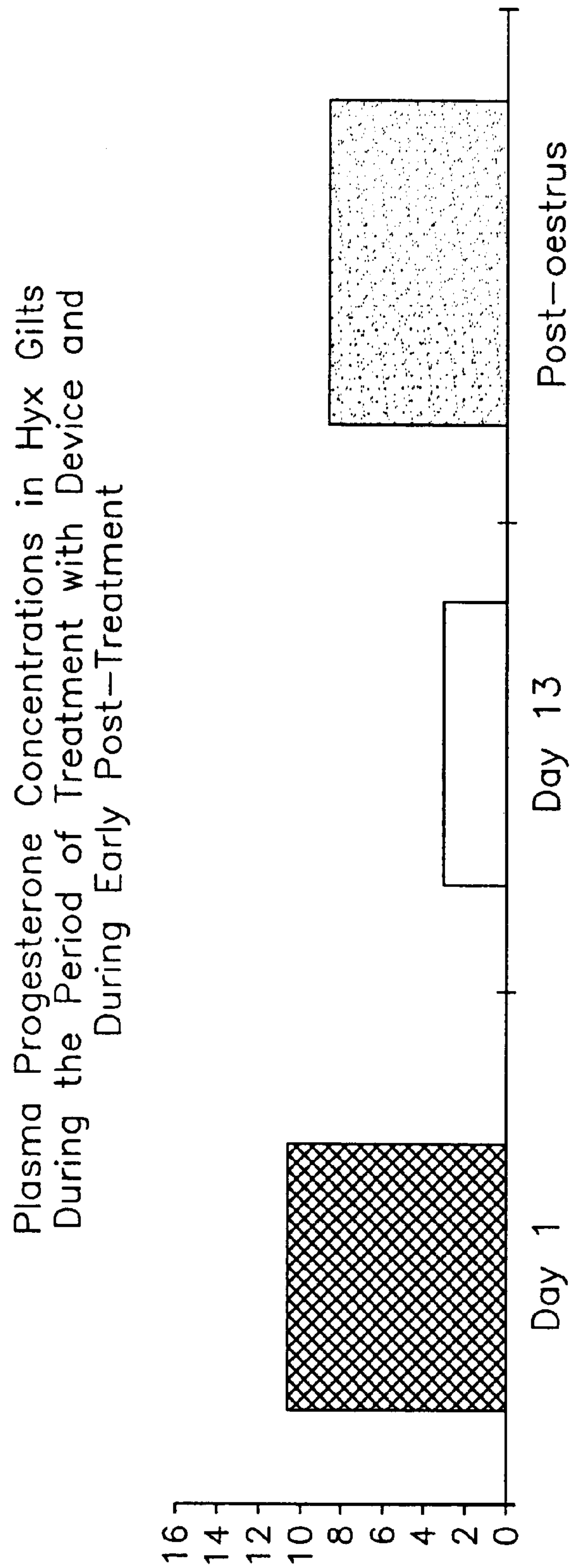
FIG. 7 is a simplified version of the plot of FIG. 6.
Figure 8:
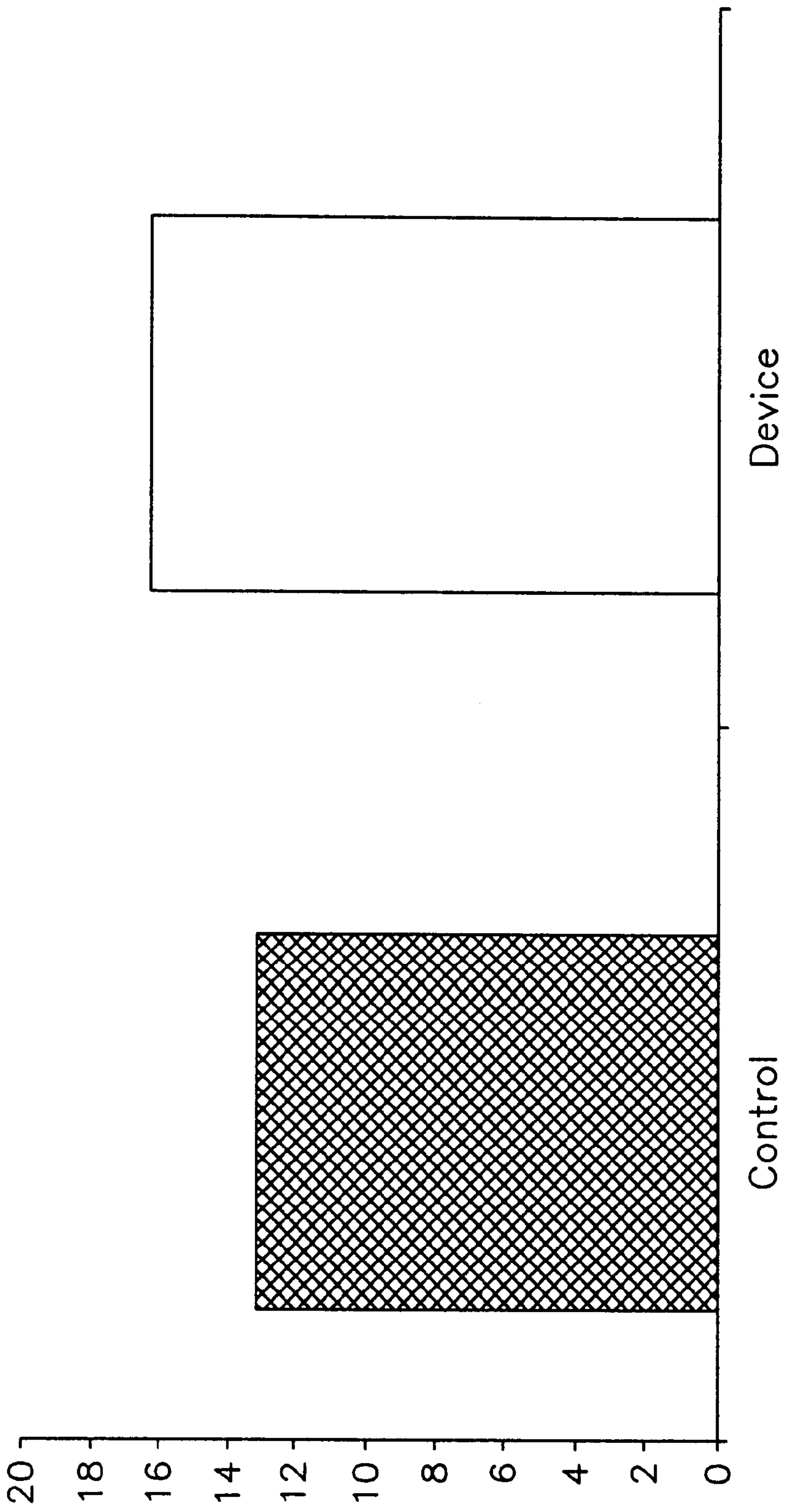
FIG. 8 shows control against the use of a device of the present invention insofar as corpora lutea numbers are concerned after a 14 day insertion period.
Figure 9:
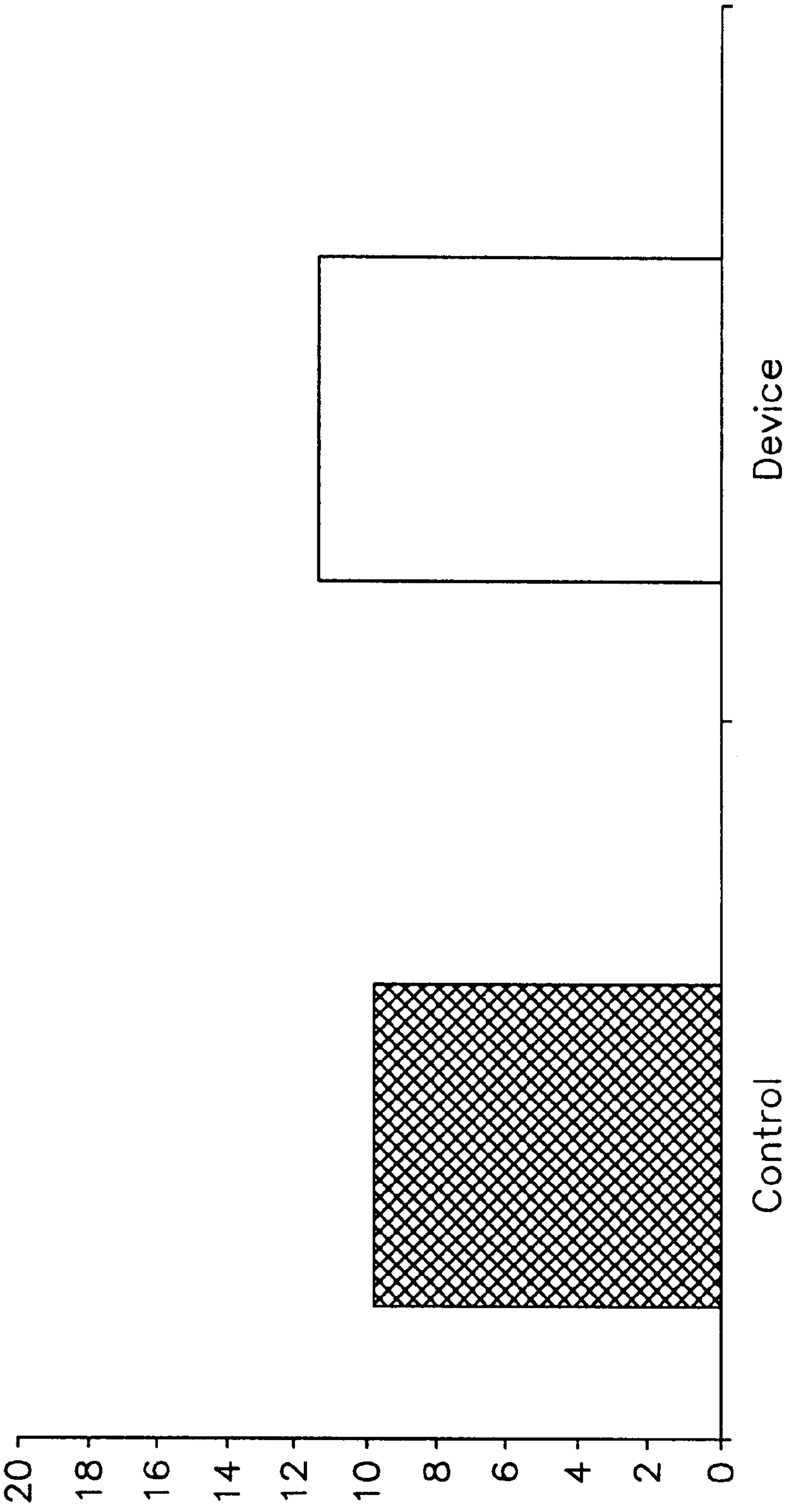
FIG. 9 shows for the same trial as FIG. 8 control against the use of the device insofar as the number of normal embryos are concerned on day 30 of pregnancy.

Plasma Data:

FIG. 6 shows progesterone plasma levels produced by the device of FIG. 1 as trialed in hysterectomised animals. Hysterectomised animals do not produce their own endogenous progesterone and hence progesterone determined in the plasma of these animals is primary from the device.

In normal cycling animals we obtained the following plasma progesterone ranges:

On day 2 after insertion of the device insertion plasma levels ranged from 4.8 to 14.5 ng/mL, control animals ranged from <0.2 ng/mL to 9.2 ng/mL).

On day 13, (1 day before the removal of the devices) plasma levels ranged from 0.9 ng/mL to 5.8 ng/mL, —control animals ranged from <0.2 ng/mL to 10.1 ng/mL).

Onset of Oestrus:

Thirteen out of fifteen animals came on heat within 3–5 days after device removal. The other three treated animals came on heat on 5, 6 and 9 days after device removal respectively. Control animals (ie; without any intra-vaginal device or other oestrus synchrony treatment) were spread throughout an 18 day range.

Fertility Data:

Table 2 shows fertility date for the device insertion experiment. Treated animals showed an average of 3.2 more corpora lutea (CL) than control (P=0.0151) and an increase of 1.4 more embryos than controls (P=0.35). See also FIGS. 6, 7, 8 and 9.

This data suggests that continuous delivery of progesterone over the 14 day treatment period can increase ovulation rate in gilts. The increase in ovulation rate appears to result in an increase in fertility rate or number of embryos.

The amount of progesterone released from the devices over the 14 day insertion period ranged from 1200 mg–900 mg.

Depletion of Progesterone from the Devices:

Depletion of progesterone from the devices occurred from the top 1.2 mm of the matrix. The initial drug load of the device was 2.7 g (with a skin [ie; impregnated matrix] thickness of 1.5 mm). The skin thickness results suggest the initial drug load could therefore be reduced to about 80% (2.2 g).

Retention:

All devices were retained for the full 14 day insertion period (100% retention). This is to be compared with 82% for the prior art devices.

TABLE 2

FETAL DATA -

| PIG No. | Days After Mating | No. CL | Live Fetuses | Dead Fetuses |
|---|---|---|---|---|
| CONTROL GILTS 1998 | | | | |
| 1 | 32 | 12 | 7 | 0 |
| 2 | 32 | 16 | 11 | 1 |
| 3 | 35 | 15 | 12 | 0 |
| 4 | 34 | 8 | 5 | 0 |
| 5 | 31 | 14 | 9 | 0 |
| 6 | 31 | 9 | 9 | 0 |
| 7 | 31 | 19 | 12 | 0 |
| 8 | 30 | 14 | 13 | 0 |
| 9 | 30 | 14 | 14 | 0 |
| 10 | 30 | 13 | 5 | 0 |
| 11 | 28 | 12 | 12 | 0 |
| Mean ± SD 13.3 ± 3.1 | 9.9 ± 3.2 | | | |
| Treated Gilts | | | | |
| 12 | 29 | 12 | 11 | |
| 13 | 31 | 18 | 5 | 0 |
| 14 | 31 | 18 | 11 | 1 |
| 15 | 31 | 17 | 12 | 0 |
| 16 | 31 | 24 | 17 | 0 |
| 17 | 31 | 15 | 15 | 0 |
| 18 | 31 | 15 | 9 | 0 |
| 19 | 30 | 17 | 15 | 0 |
| 20 | 30 | — | — | — |
| 21 | 30 | 14 | 10 | 1 |
| 22 | 30 | 14 | 7 | 0 |
| 23 | 31 | 16 | 11 | 1 |
| 24 | 29 | 14 | 9 | 0 |
| 25 | — | — | — | - |
| 26 | 31 | 16 | 14 | 0 |

M ± SD 16.5 ± 2.8 11.3 ± 3.6
Mean difference
3.2 CL 1.4 embryos
P = 0.0151 P = 0.35

What is claimed is:

1. A porcine intra-vaginal device having a shape and a size that extends to both sides of the hymenal ring of the female pig, wherein the device comprises a matrix or matrices having a progesterone load of at least 1.9 g and is at least 150 $cm^3$ in total area.

2. The device of claim 1 wherein said total area of the matrix or matrices is greater than 180 $cm^2$.

3. The device of claim 1 wherein said progesterone load is from 1.9 to 2.5 g.

4. The device of claim 1 wherein the female pig is a gilt and said progesterone load is about 2.2 g.

5. The device of claim 1 wherein said progesterone load is at least substantially all carried by the matrix or matrices within 1.2 mm of its release surface.

6. The device of claim 1 wherein the device has a spine with a progesterone impregnated silicone rubber matrix formed thereabout.

7. The device of claim 6 wherein the rubber matrix has been formed by injection of an uncured progesterone containing matrix as a liquid into a mould for a sufficient time to achieve a mould temperature or temperatures within the range of 100° C. to 210° C. and a shape retaining at least a partial cure thereof.

8. A device claim 1 wherein the device has variable geometry means which deploy or are deployed upon insertion to retain the device in the vaginal tract.

9. A device of claim 8 wherein the variable geometry means comprise at least one resilient wing or a form collapsible under the action of withdrawal.

10. A device of claim 1 wherein the device is elongate of body with a wasted region to lie on the hymenal ring.

11. A porcine intra-vaginal device having a shape and a size that extends to both sides of the hymenal ring of the female pig, wherein the device comprises a progesterone impregnated matrix or matrices and a variable geometry means which deploy in the vestibule upon insertion to retain the device in the vaginal tract.

12. A device of claim 11 wherein said matrix or matrices are at least 150 $cm^2$ in total area.

13. A device of claim 12 wherein said total area of progesterone impregnated matrix or matrices is greater than 180 $cm^2$.

14. A device of claim 13 wherein said matrix or matrices carry a progesterone load of at least 1.9 g.

15. A device of claim 14 wherein said progesterone load is from 1.9 to 2.5 g.

16. The device of claim 15 wherein the female pig is a gilt and said progesterone load is about 2.2 g.

17. A device of claim 14 wherein said progesterone load is at least substantially all carried by the matrix or matrices within 1.2 mm of its release surface.

18. The device of claim wherein the device has a spine with a progesterone impregnated silicone rubber matrix formed thereabout.

19. The device of claim 18 wherein the silicone rubber matrix has been formed by injection of an uncured progesterone containing matrix as a liquid into a mould for a sufficient time to achieve a mould temperature or temperatures within the range of 100° C. to 210° C. and a shape retaining at least a partial cure thereof.

20. An intra-vaginal device having a shape and size that extends to both sides of the hymenal ring of a female pig comprising a body to be inserted in the female pig with part of the body on either side of the hymenal ring of the female pig and a variable geometry retention means depended from the part of the body to be located in the vestibule of the vaginal tract, said variable geometry retention means being capable of assuming a vestibular engagement form after release from an insertion mode.

21. A device of claim 20 wherein the body is not articulated.

22. The device of claim 20 wherein said vestibule geometry retention means is or are capable of assuming a third mode upon the application of an external force to part of said device within said vestibule or to any means dependent therefrom extending towards, through, or both the vulva.

23. A device of claim 20 wherein said variable geometry retention means is in the form of wing members.

24. The device of claim 23 wherein said wing members assume in their vestibular engagement mode a condition such that spasm of the vestibular wall of the female pig into which the device has been inserted is unlikely to provide a sufficient component of force on the inserted device to cause ejection from the vaginal tract.

25. The device of claim 20 wherein said variable geometry retention means in said vestibular engagement mode engages into folds at least momentarily present in the vestibule wall of the female pig into which it has been inserted.

26. The device of claim 20 wherein the variable geometry retention means is such that spasm of the vaginal tracts provides no significant net force away from the cervix on the device.

27. The device of claim 23 further comprising two wing members, each of which, in its deployed vestibular engagement mode, has a distal end closer to the vulva than the part of the body of the device from which wing member projects.

28. A device of claim wherein said wing members lie in the same plane.

29. The device of claim 20 wherein the device includes a reduced section or an effective reduced section over that region of the body of the device adjacent the variable geometry retention means dependent therefrom but which is adapted to lie within the hymenal ring of the female pig when the device is in its retained condition.

30. A device of claim 20 wherein the device or at least parts thereof carries or is a matrix impregnated with or carrying a substance to be released to the animal.

31. A device of claim 20 wherein the construction of the device is such that it does not extend into the cervix during normal insertion operations and such that upon normal insertion where it is retained by said variable geometry retention means such variable geometry retention means and/or the configuration of the elongate body of the device is such as to prevent sufficient movement through the hymenal ring to allow the end of the device to enter the cervix.

32. A device of claim 20 wherein that part of the elongate body which carries the variable geometry retention means includes means capable of being engaged by a device withdrawal tool.

33. An intra-vaginal device for delivering a substance into a female pig having a shape and size that extends to both sides of the hymenal ring of the female pig comprising a body having a withdrawal end and an insertion end and capable of traversing the hymenal ring of the pig with the withdrawal end in the vestibule and the insertion end in the vaginal cavity, and at least one wing like structure capable of self deployment from an insertion condition into a membrane engaging condition to resist spontaneous ejection of the device, the membrane being selected from one or more of (i) vestibular membrane, (ii) hymenal ring membrane, and (iii) vaginal membrane.

34. A device of claim 20 where the device includes from 1.9 to 2.5 grams of progesterone.

35. A device of claim 34 wherein the progesterone loading is about 2.0.

36. The device of claim 34 wherein the device is capable of maintaining a progesterone blood plasma level equating to a progesterone blood plasma level in excess of 4 ng/mL measured in an ovarectomised female pig, over a period of 7 to 14 days in an average gilt being prepared for the onset of oestrus upon withdrawal of the device.

37. An intra-vaginal device for delivering a substance into a pig comprising a body having a withdrawal end and an insertion end and capable of traversing the hymenal ring of the pig with the withdrawal end in the vestibule and the insertion end in the vaginal cavity, and at least one wing like structure capable of self deployment from an insertion condition into a membrane engaging condition to resist spontaneous ejection of the device, the membrane being selected from one or more of (i) vestibular membrane, (ii) hymenal ring membrane, and (iii) vaginal membrane.

38. A pack which includes a plurality of intra-vaginal devices as claimed in claim 1 and, optionally, at least one applicator and/or withdrawal tool therefor.

39. A method of delivering a substance into a female pig which comprises inserting a device as claimed in claim 1 into the vaginal tract of the pig so as to release a substance from the device whilst resident therein, the device resisting spontaneous ejection by means of the deployment of said variable geometry retention means within the vestibule so as to engage the wall or walls thereof.

40. A method of claim 39 wherein said device is inserted in a female pig for a period of from 7 to 18 days where it maintains substantially over its insertion period a blood plasma level of progesterone equating to a progesterone blood plasma level in excess of 4 ng/mL measured in an ovarectomised animal and whereupon, upon its withdrawal, will ensure or prompt within 3 to 5 days thereafter the onset of oestrus in that pig.

41. A method claim 40 wherein the withdrawal is achieved by hooking a tool wire or other apparatus into the vestibular end region of the device and withdrawing the same.

* * * * *

UNITED STATES PATENT AND TRADEMARK OFFICE

CERTIFICATE OF CORRECTION

PATENT NO. : 6,444,224 B1
DATED : September 3, 2002
INVENTOR(S) : Rathbone et al.

It is certified that error appears in the above-identified patent and that said Letters Patent is hereby corrected as shown below:

<u>Column 12,</u>
Lines 45-46, change "150 $cm^3$" to -- 150 $cm^2$ --.

Signed and Sealed this

Sixteenth Day of May, 2006

JON W. DUDAS
*Director of the United States Patent and Trademark Office*